United States Patent
Zhang

(10) Patent No.: US 8,480,995 B2
(45) Date of Patent: Jul. 9, 2013

(54) USE OF SODIUM SELENOSULFATE FOR SUPPLEMENTING SELENIUM AND ENHANCING THE THERAPEUTIC EFFICACY OF CHEMOTHERAPY AGENTS, AND A RAPID PROCESS FOR PREPARING SODIUM SELENOSULFATE

(75) Inventor: Jinsong Zhang, Hefei (CN)

(73) Assignee: University of Science and Technology of China, Anhui (CN)

( * ) Notice: Subject to any disclaimer, the term of this patent is extended or adjusted under 35 U.S.C. 154(b) by 537 days.

(21) Appl. No.: 12/452,014

(22) PCT Filed: Jun. 11, 2008

(86) PCT No.: PCT/CN2008/001131
§ 371 (c)(1),
(2), (4) Date: Mar. 23, 2010

(87) PCT Pub. No.: WO2008/151520
PCT Pub. Date: Dec. 18, 2008

(65) Prior Publication Data
US 2010/0172822 A1    Jul. 8, 2010

(30) Foreign Application Priority Data

Jun. 13, 2007  (CN) .......................... 2007 1 0023256

(51) Int. Cl.
*A61K 33/04*   (2006.01)
*A61P 35/00*   (2006.01)
*C01B 19/00*   (2006.01)
*A61P 3/02*    (2006.01)

(52) U.S. Cl.
USPC ........................................................ 423/508

(58) Field of Classification Search
None
See application file for complete search history.

(56) References Cited

U.S. PATENT DOCUMENTS 4,617,189 A * 10/1986 Stockel et al. ................ 424/702
2006/0105960 A1* 5/2006 Erdelmeir et al. .............. 514/18

FOREIGN PATENT DOCUMENTS

| CN | 1415308 | 5/2003 |
| CN | 1443707 | 9/2003 |
| CN | 1449768 | 10/2003 |
| GB | 2283677 | 5/1995 |
| WO | WO 2005013951 | 2/2005 |

OTHER PUBLICATIONS

Peng et al., Biological Trace Element Research, 117: 77-88, Cover date, Jun. 1, 2007.*
Zhang et al., Toxicology and Applied Pharmacology, 226: 251-259 (2008), published on-line Sep. 19, 2007.*
Zhang et al., Biological Trace Element Research, 125: 12-21 (2008), published on-line Oct. 24, 2007.*
PubMed citation for Peng et al., Biological Trace Element Research, 117:77-88 (2007), accessed at http://www.springerlink.com/content/ul8j4h68u6021765/export-citation/, Sep. 4, 2012.*
Date Stamp, National Library of Medicine, Biological Trace Element Research, 117(1-3) cover. (Sep. 7, 2007).*
International Search Report for PCT/CN2008/001131 mailed Sep. 18, 2008.

* cited by examiner

*Primary Examiner* — Daniel Sullivan
*Assistant Examiner* — Lisbeth C Robinson
(74) *Attorney, Agent, or Firm* — Nixon & Vanderhye P.C.

(57) ABSTRACT

The present invention relates to a use of sodium selenosulfate for supplementing selenium and enhancing the therapeutic efficacy of chemotherapy agents for cancers, and a rapid process for preparing sodium selenosulfate comprising: mixing sodium selenite, the reducing agent and sodium sulfite in a certain proportion to form sodium selenosulfate quickly.

8 Claims, 5 Drawing Sheets

Chemical structure of sodium selenosulfate and sodium selenite

Sodium selenosulfate

Sodium selenite

Fig. 1   Chemical structure of sodium selenosulfate and sodium selenite
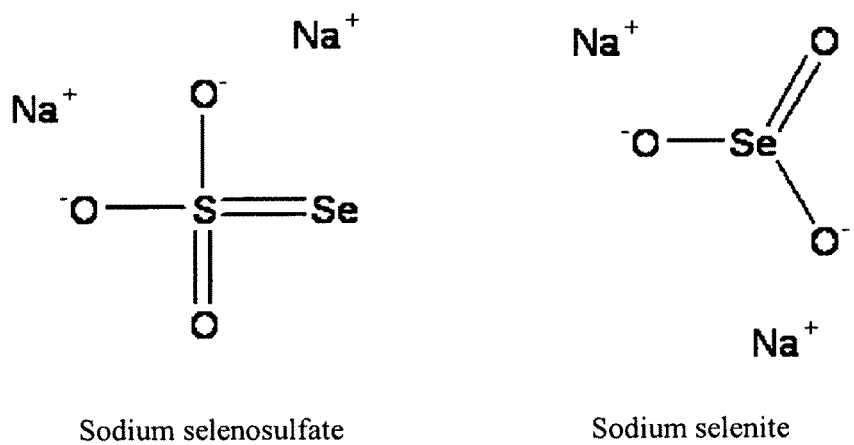
Sodium selenosulfate            Sodium selenite
Fig. 2   The average body weights of the mice
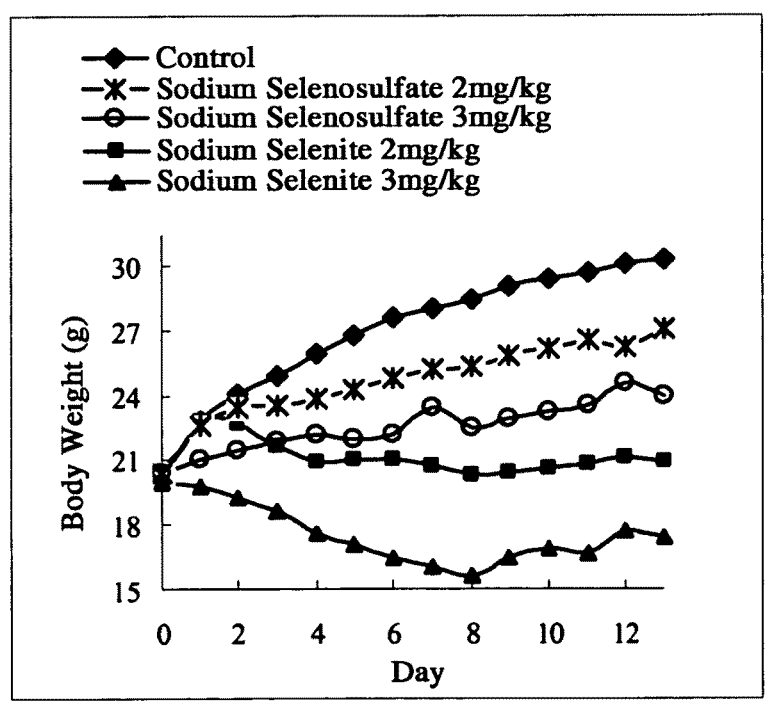

Fig. 3 The survival curves of the mice
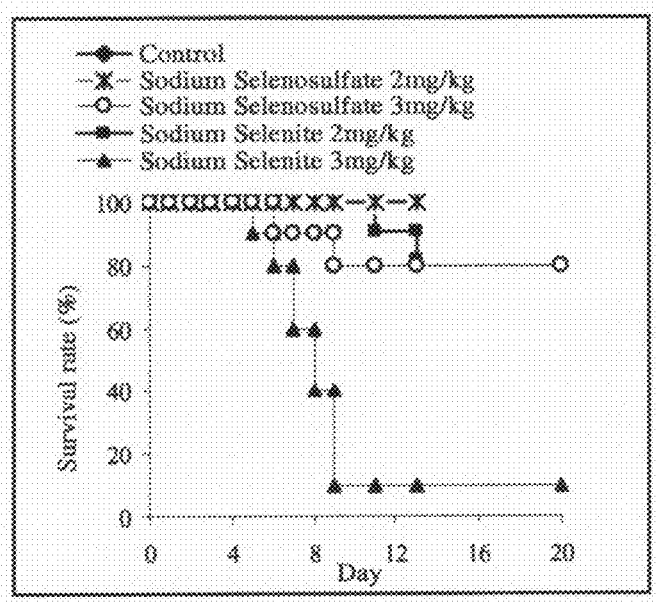
Fig. 4 The changes of serum alanine aminotransferase (ALT) and aspartate aminotransferase (AST)
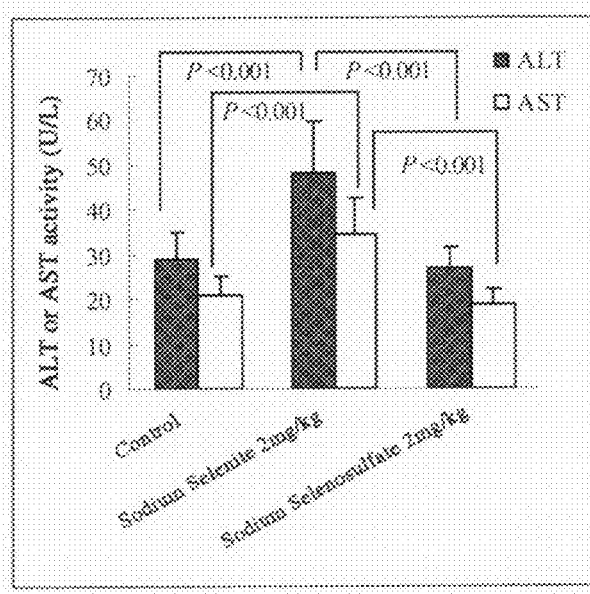

Fig. 5 Hepatic tissue slice after sodium selenite treatment
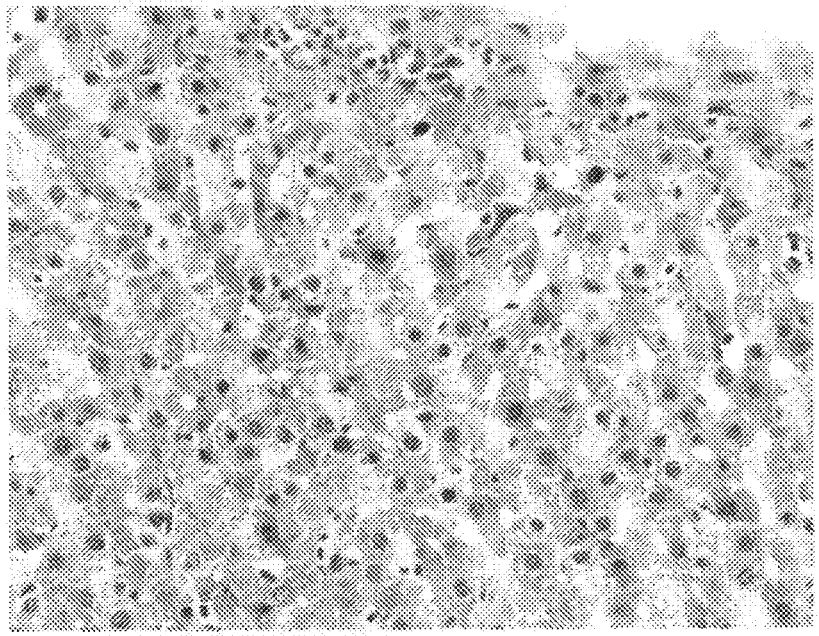
Fig. 6 Hepatic tissue slice after sodium selenosulfate treatment
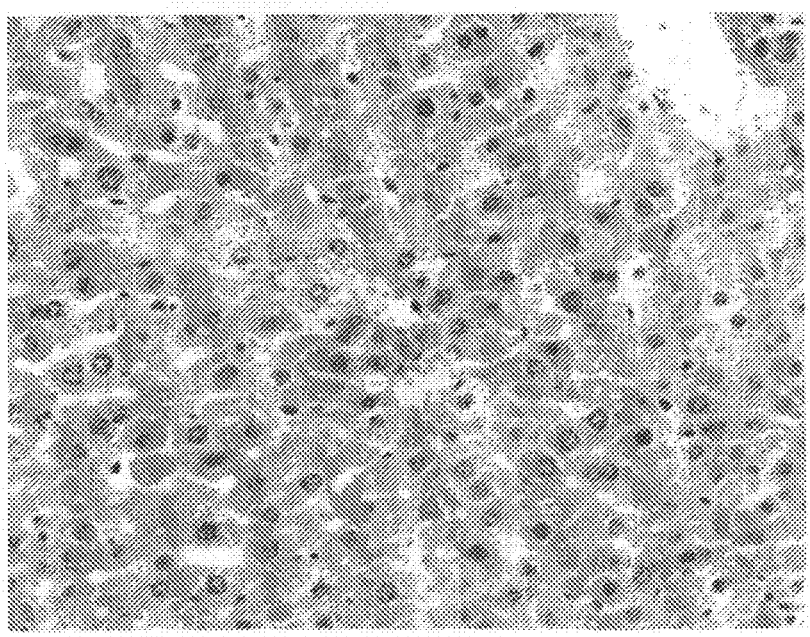

Fig. 7 Killing effect (A) and the growth suppressing effect (B) of selenium on HepG2 tumor cells
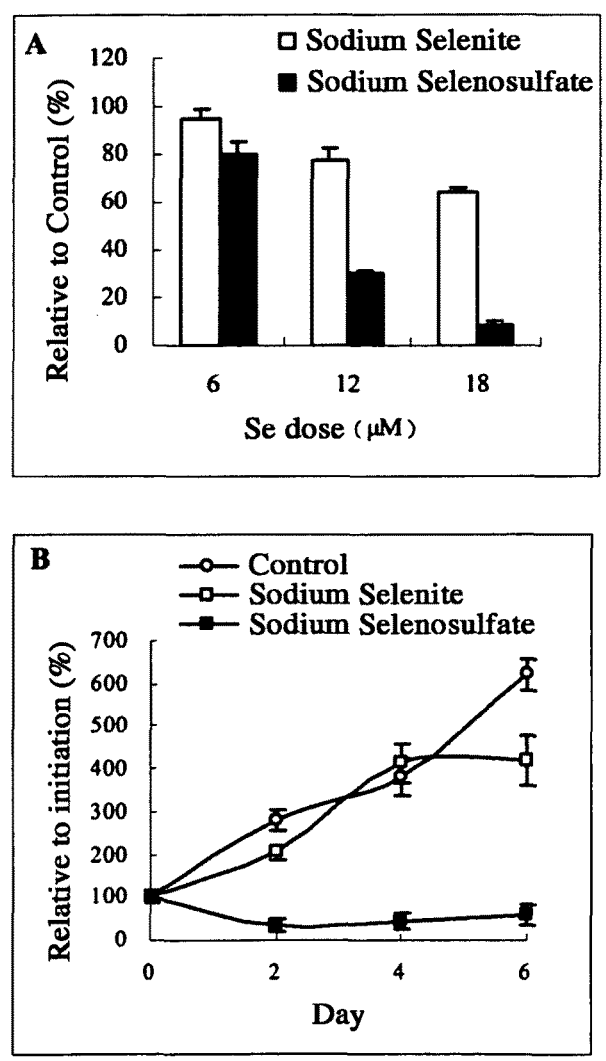

Fig. 8 Killing effect (A) and the growth suppressing effect (B) of selenium on CaCo2 tumor cells
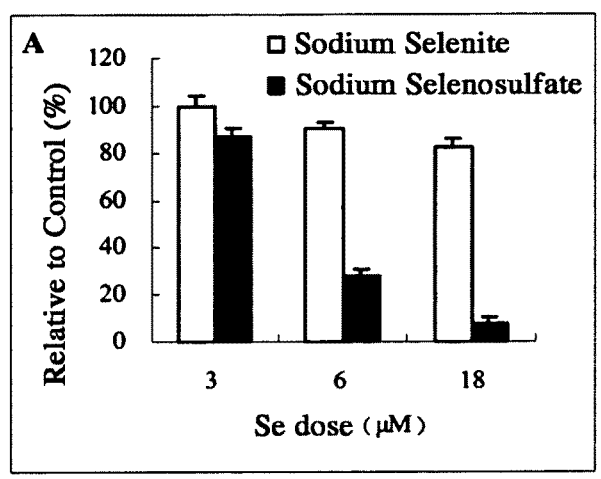
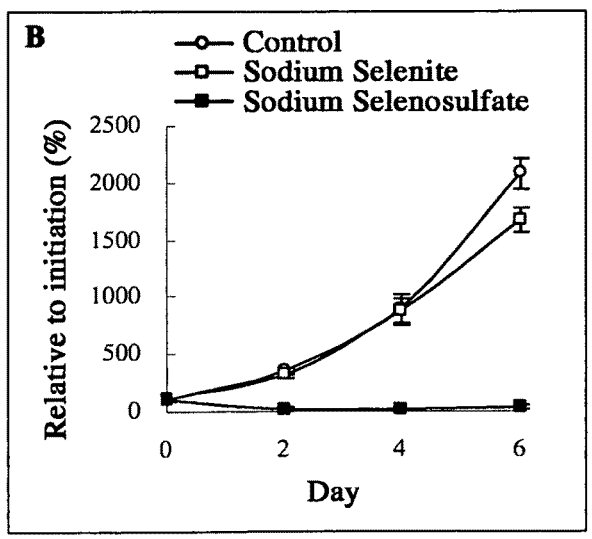

United States Patent US 8,480,995 B2

USE OF SODIUM SELENOSULFATE FOR SUPPLEMENTING SELENIUM AND ENHANCING THE THERAPEUTIC EFFICACY OF CHEMOTHERAPY AGENTS, AND A RAPID PROCESS FOR PREPARING SODIUM SELENOSULFATE

This application is the U.S. national phase of International Application No. PCT/CN2008/001131 filed 11 Jun. 2008 which designated the U.S. and claims priority to Chinese Patent Application No. 200710023256.4 filed 13 Jun. 2007, the entire contents of each of which are hereby incorporated by reference.

FIELD OF THE INVENTION

The present invention relates to a new use of sodium selenosulfate, in particular, to a use of sodium selenosulfate for supplementing selenium and enhancing the therapeutic efficacy of chemotherapy agents for cancers, and a rapid process for preparing sodium selenosulfate.

BACKGROUND OF THE INVENTION

Selenium is an essential trace element for human body. Selenocysteine is the active site of glutathione peroxidase, phospholipid-hydroperoxide glutathione peroxidase, thioredoxin reductase, methionine sulfoxide reductase and indothyronine deiodinase, and participates in the antioxidation and energy metabolism of the organism. In addition, high doses of selenium has growth suppressing and killing activities on tumor cells.

It has been known that the survival situation of the patient in the Intensive Care Unit was significantly improved by injecting high doses of sodium selenite, and the death rate is reduced largely. Since sodium selenite is a selenium compound with strong toxicity, and the margin between the beneficial dose and the toxic dose is quite narrow, there is a need in clinic to replace sodium selenite with a different selenium form, which has the same bioactivity to high doses of sodium selenite but with lower toxicity.

Chemotherapy may result in side effects such as leucocyte reduction, diarrhea, vomit, edema and the like and even threaten the life of the patients. These side effects seriously restrict the dosage and therapeutic efficacy of chemotherapy agents. It has been reported that sodium selenite can depress the toxicity of cisplatin without compromising its activity, which makes it possible to use high doses of cisplatin to enhance the anti-tumor effect of cisplatin. However, the doses of sodium selenite in these studies were all in the toxic level (0.5-2 mg Se/kg), and the therapeutic efficacy will be attenuated after long-term co-administration of sodium selenite and chemical agents. Since the margin between the beneficial and toxic dose of selenium is quite narrow, only selenium compounds with lower toxicity can ensure the safe application for supplementing selenium at pharmacologic doses and treating tumors with the co-administration of chemical agents.

Sodium selenosulfate is an unstable inorganic selenium compound, and thus does not have a commercially available product. It was used widely for the preparation of nanomaterials containing selenium. For example, sodium selenosulfate was used to prepare nano-sized copper selenide, cadmium selenide, lead selenide and the like. Generally, sodium selenosulfate was prepared by mixing elemental selenium power with sodium sulfite with a molar ratio of 1:3 to 1:6 and refluxing at a temperature of 80-100° C. for 2-4 hours. It is of prime importance for the stable time of the newly generated sodium selenosulfate that the sodium sulfite presents in excess, and the more sodium sulfite presents, the longer the stable time is. In general, the newly generated sodium selenosulfate is used immediately for the preparation of selenium nanomaterials. Sodium selenosulfate is a selenium compound, and there is no any report as to its Se-supplementing effect and biological functions related to selenium.

SUMMARY OF THE INVENTION

In order to overcome the problem about selenium toxicity, the present invention is tried to find a safer selenium compound, which can be used to replace sodium selenite.

The present invention provides a new use of sodium selenosulfate, in particular, the use of sodium selenosulfate for supplementing selenium and enhancing the therapeutic efficacy of chemotherapy agents for cancers.

It is proved in the present invention that sodium selenosulfate and sodium selenite possess equal efficacy in selenium supplement at pharmacologic doses. FIG. 1 shows the chemical structure of the two compounds. It is of interest that sodium selenosulfate shows much lower toxicity to normal tissue, but much higher toxicity to tumor cells as compared with sodium selenite, which shows the rationality for using sodium selenosulfate.

The present invention proves that sodium selenosulfate has the same efficacy for supplementing selenium at pharmacologic doses but with significant lower toxicity as compared with sodium selenite, and is able to efficiently attenuate the toxicity of chemotherapy agents and significantly improve their cure rates. These properties show the necessity of its application. However, sodium selenosulfate is unstable, which is the problem encountered in the long-term administration of sodium selenosulfate in clinic for supplementing selenium and improving the therapeutic efficacy of chemotherapy agents. Thus it is required that sodium selenosulfate should be prepared immediately prior to use. However, in the prior art, sodium selenosulfate is prepared by mixing elemental selenium powder with sodium sulfite, and refluxing a few hours at a high temperature. Obviously, this process is not suitable for clinic use. To obtain sodium selenosulfate conveniently, the present invention provide a rapid process for preparing sodium selenosulfate by mixing sodium selefite, a reductive agent and sodium sulfite in a certain proportion.

The detailed rapid preparative process comprises: mixing sodium selefite, a reductive agent and sodium sulfite in a certain proportion.

In one embodiment of the process of the present invention, sodium selenite was reduced by a reductive agent having a mercapto group. The reductive agent may be selected from the group consisting of glutathione, cysteine, N-acetylcysteine, lipoic acid and the like. It was mixed with sodium selenite to form RS—Se—SR, which is stable under acidic condition and converted to elemental selenium under neutral or alkaline condition. After sodium sulfite was added into the mixture of sodium selenite and the reductive agent, the RS—Se—SR was converted to elemental selenium due to the alkalescence of sodium sulfite. Then sodium sulfite rapidly reacted with the newly generated elemental selenium to form sodium selenosulfate immediately.

In another embodiment of the process of the present invention, sodium selenite was reduced by a reductive agent without a mercapto group, such as antiscorbic acid, sulfur dioxide, etc. The reductive agent was mixed with sodium selenite to form elemental selenium. After sodium sulfite was added to the mixture of sodium selenite and the reductive agent, it rapidly reacted with the elemental selenium to form sodium selenosulfate.

These processes can ensure to obtain fresh sodium selenosulfate easily and rapidly so as to easily apply sodium selenosulfate in clinic for supplementing selenium or improving the therapeutic efficacy of chemotherapy agents.

BRIEF DESCRIPTION OF THE DRAWINGS

FIG. 1 is a scheme illustrating the chemical structure of sodium selenosulfate and sodium selenite;

FIG. 2 is a graph showing the average body weights of the mice;

FIG. 3 is a graph showing the survival curves of the mice;

FIG. 4 is a graph showing the changes in the activities of serum alanine aminotransferase (ALT) and aspartate aminotransferase (AST);

FIG. 5 is a micrograph of a hepatic tissue slice after sodium selenite treatment;

FIG. 6 is a micrograph of a hepatic tissue slice after sodium selenosulfate treatment;

FIG. 7 is a graph showing the killing effect (A) and the growth suppressing effect (B) of selenium on HepG2 tumor cells; and FIG. 8 is a graph showing the killing effect (A) and the growth suppressing effect (B) of selenium on CaCo2 tumor cells.

DETAILED DESCRIPTION

Best Mode for Carrying Out the Invention

Hereinafter, the present invention will be described in detail by examples in reference to the accompanying drawings.

Example 1

Comparison of the Se-Supplementing Effect Between Sodium Selenosulfate and Sodium Selenite at Pharmacologic Doses It has been reported that high doses of sodium selenite can reduce the symptom of severely ill patient and enhance the therapeutic efficacy of chemotherapy agents for cancers. It remains unknown whether there are differences regarding the Se-supplementing effect between sodium selenosulfate and sodium selenite at pharmacologic doses. In this example, Se-deficient mice were intraperitoneally injected with sodium selenite and sodium selenosulfate at doses of 0.5 and 1 mg Se/kg for a week. The enzyme activity and selenium were measured to compare the Se-supplementing effect between the two selenium compounds.

Animals: Se-deficient male Kunming mice (body weight: 20-23 g) were purchased from the animal center of Anhui Medical University. Drugs Administration: 35 mice were randomly divided into 5 groups with 7 mice in each group. The mice in the control group were injected with normal saline, and those in other groups were injected respectively with different doses of sodium selenite and sodium selenosulfate (0.5 and 1 mg Se/kg) for 7 consecutive days. Biochemical parameters: 24 hours after the last Se administration, blood was sampled from ophthalmic veins to obtain serum by centrifugation, and then the Se form and glutathione peroxidase (GPx) activity therein were determined. Meanwhile, liver and kidney were excised and stored at −30° C., and a part of them were used to determine Se. A part of livers and kidneys were homogenized and centrifuged to obtain supernatant, and then GPx activity and glutathione S-transferase (GST) activity in livers were determined. Statistical analysis: Data were expressed as mean±SD. The differences between the groups were examined using ANOVA. A p value less than 0.05 was considered statistically significant.

Results and discussion: The results are summarized in Table 1. It can be seen that both sodium selenosulfate and sodium selenite can efficiently increase the Se-level, GPx activity and GST activity in the tissues, and no difference was observed between their bioactivities at the pharmacologic doses. Therefore, if high doses of Se are needed clinically, sodium selenosulfate has the same efficiency as sodium selenite. Obviously, the key is whether they have difference in their toxicities, because the pharmacologic dose of Se is very close to the toxic dose, and even some pharmacologic doses have toxic consequence.

TABLE 1

Comparison of the bioactivity between sodium selenosulfate and sodium selenite at pharmacologic doses

| Biochemical parameters | Control | Sodium selenosulfate 0.5 mg/kg | Sodium selenite 0.5 mg/kg | Sodium selenosulfate 1.0 mg/kg | Sodium selenite 1.0 mg/kg |
|---|---|---|---|---|---|
| Serum Se | 1.00 ± 0.06 | 5.69 ± 0.13 | 5.02 ± 0.15 | 5.24 ± 0.39 | 5.41 ± 0.29 |
| Liver Se | 1.00 ± 0.27 | 11.2 ± 0.09 | 10.9 ± 0.18 | 15.2 ± 0.09 | 15.4 ± 0.09 |
| Kidney Se | 1.00 ± 0.19 | 2.85 ± 0.10 | 2.83 ± 0.10 | 3.90 ± 0.14 | 3.50 ± 0.12 |
| Serum GPx | 1.00 ± 0.22 | 3.10 ± 0.25 | 2.97 ± 0.37 | 4.41 ± 0.24 | 4.18 ± 0.26 |
| Liver GPx | 1.00 ± 0.36 | 18.8 ± 0.19 | 19.8 ± 0.08 | 22.2 ± 0.16 | 22.2 ± 0.10 |
| Kidney GPx | 1.00 ± 0.17 | 7.74 ± 0.19 | 8.74 ± 0.14 | 9.09 ± 0.18 | 10.2 ± 0.14 |
| Liver GST | 1.00 ± 0.15 | 1.47 ± 0.29 | 1.64 ± 0.23 | 2.69 ± 0.23 | 2.44 ± 0.14 |

Notes:

The control Se level in serum, liver and kidney was 0.07 μg/mL serum, 0.15 μg/g liver and 0.44 μg/g kidney respectively.

The control GPx activity in serum, liver and kidney was 525.5 unit/mL serum, 88.5 unit/mg protein and 142.8 unit/mg protein respectively.

The control GST activity in liver was 4071.4 unit/mg protein.

Example 2

Comparison of the Toxicity to Normal Tissues Between Sodium Selenosulfate and Sodium Selenite Animals: Se-sufficient male Kunming mice (body weight: 23±1 g) were purchased from the Shanghai Laboratory Animal Center, Chinese Academy of Sciences. Drugs Administration: 50 mice were randomly divided into 5 groups with 10 mice in each group. The mice in the control group were injected intraperitoneally with normal saline, and the other groups were injected with sodium selenite (2 groups) and sodium selenosulfate (2 groups) respectively at 2 and 3 mg Se/kg once daily for 14 consecutive days. The mice in low dosage groups were sacrificed 24 hours after the last Se administration. Animal status: The body weight and dead status of the mice were recorded every day. Biochemical parameters: Blood was sampled from ophthalmic veins for determining serum ALT activity and AST activity. Pathology: Liver was excised for the determination. The slice was dyed by using HE. Statistical analysis: Data were expressed as mean±SD. The differences between the groups were examined using ANOVA. A p value less than 0.05 was considered statistically significant.

Results and discussion: It can be seen from FIG. 2 that high doses of Se could suppress the growth of the mice as compared with the control, and the suppression of sodium selenite was significantly stronger than that of sodium selenosulfate at the same Se levels. FIG. 3 shows that, at 2 mg Se/kg, sodium selenite resulted in 20% mortality, whereas all the mice treated with sodium selenosulfate survived; at 3 mg Se/kg, sodium selenite resulted in 90% mortality, whereas sodium selenosulfate resulted in only 20% mortality, and the deference was significant between the two Se groups with $p<0.001$. FIG. 4 shows that 2 mg Se/kg of sodium slenite resulted in obvious hepatotoxicity and made ALT and AST increased significantly, whereas such phenomenon was not found in the mice treated with sodium selenosulfate, which had significant difference from the sodium selenite groups (all $p<0.001$). FIG. 5 shows that 2 mg Se/kg of sodium selenite resulted in obvious hepatotoxicity and caused moderate hydropic or fatty degeneration in up to 80% of the pathoslice and partial punctiform necrosis. FIG. 6 shows that sodium selenosulfate treatment only induced slight hydropic degeneration in 20% of the liver slice. All these results showed that sodium selenosulfate caused a lower toxicity to normal tissues than sodium selenite.

Clinically, the supplement of high doses of Se may improve the activity of Se-containing enzyme such as GPx, which can remove the excess hydrogen peroxide, and thus maintain the antioxidation balance in the organism. High doses of Se may also induce the phase II/detoxifying enzymes such as GST in the organism, which can detoxify the toxic substances and remove fatty peroxide to perform detoxification and maintain the antioxidation balance in the organism. High doses of Se may inhibit the transcription factor (NF-κB) related to inflammation, reduce its transcription efficiency, and decrease the levels of the inducible nitric oxide synthase and inducible cyclooxygenase, so as to reduce the levels of small molecules such as nitrogen oxide and prostaglandin which are related to inflammation, and thus play the anti-inflammatory function. Therefore, the supplementation of high doses of sodium selenite has good effects for critically ill patients on the improvement of their survival status and reduction of the death rate. It can be seen from Table 1 that sodium selenite and sodium selenosulfate have the same ability in the supplementation of selenium and the improvement of GPx and GST activities at the pharmacologic doses. Obviously, it is safer to use sodium selenosulfate clinically to supplement Se at pharmacologic doses.

Example 3

Comparison of the Toxicity to Tumor Cells Between Sodium Selenosulfate and Sodium Selenite Cell culture: Human hepatoma cells (HepG2) and human colorectal cancer cells (CaCo2) were cultivated at 37° C. under 5% $CO_2$ by using EMEM cell culture media containing 10% Fetal Bovine serum. Cell killing assay: the tumor cells were added into a 96-well plate with a density of 5000 cells/well for 24 hours, and then the culture media were changed to those with different Se concentrations. At 72 hours, the cell numbers were determined by MTT protocol. Each treatment was conducted in 3 parallels, and the data were expressed by percent relative to cell numbers when no Se was added. Cell proliferation assay: HepG2 or CaCo2 cells were added into a 96-well plate with a density of 1000 cells/well for 24 hours, and then the culture media were changed to those with 12.5 µM Se. The day was defined as day 0. The cell numbers were determined by MTT protocol on day 0, 2, 4 and 6, respectively. Each treatment was conducted with 8 parallels, and the data were expressed with percent relative to the cell numbers on day 0. MTT assay: Each well was added with 20 µL MTT (5 mg/mL) 4 hours prior to the end of culture. After the culture was ended, the supernatant was discarded, and the formazan particles were dissolved in HCl-isopropanol (10 µL/well). The readings were recorded at 595 nm on a microplate reader.

Results and discussion: Sodium selenosulfate showed a dose-dependent profile on killing HepG2 cells at levels of 6-18 µM, whereas sodium selenite had a much lower effect than sodium selenosulfate (FIG. 7A). Sodium selenosulfate at the level of 12.5 µM fully suppressed the proliferation of HepG2 cells, whereas sodium selenite did not show obvious effect (FIG. 7B). The similar results were observed in CaCo2 cells (FIGS. 8A and 8B). All these results showed that sodium selenosulfate had a much stronger cytotoxicity to tumor cells than sodium selenite. Based on the above results, it can be seen that sodium selenosulfate had a lower toxicity, the same ability for supplementing selenium at pharmacologic doses, and higher activity on suppressing and killing tumor cells, as compared with sodium selenite, which demonstrated that it is a better Se form for supplementing selenium than sodium selenite.

Example 4

Improvement of the Therapeutic Efficacy of Chemotherapy Agents for Cancers by Sodium Selenosulfate Animals: Se-sufficient male Kunming mice (body weight: 20-23 g) were purchased from Shanghai Laboratory Animal Center, Chinese Academy of Sciences. Drugs Administration: 48 mice were divided randomly into 6 groups with 8 mice in each group. Each mouse was inoculated intraperitoneally with hepatoma H22 cell suspension ($20 \times 10^6$ cells). The groups were classified into 3 cisplatin groups, 2 cisplatin plus Se-supplementing groups (the groups administrated with 8 and 10 mg/kg doses of cisplatin were treated with 0.6 and 0.75 mg Se/kg doses of sodium selenosulfate, respectively) and 1 control group in terms of the administration doses (5, 8 and 10 mg/kg) of cisplatin. The experiments were carried out with one week as a cycle. The experiments with cisplatin doses of 5 and 8 mg/kg were carried out for total 4 cycles, and those with cisplatin dose of 10 mg/kg were performed for total 3 cycles. From the first day of each cycle, the mice in cisplatin groups was intraperitoneally injected with the corresponding concentrations of cisplatin, and the mice in cisplatin plus Se-supplementing groups were injected intraperitoneally with the corresponding sodium selenosulfate doses of 0.6 and 0.75 mg Se/kg respectively 4 hours before the intraperitoneal injection of cisplatin. The treatment was performed for 5 consecutive days. The first cisplatin chemotherapy started at 48 hours after the inoculation of tumor cells. The animal status was recorded and the development of malignant ascites was observed. Statistical analysis: Data were expressed as mean±SD. The differences between the groups were examined using ANOVA. A p value less than 0.05 was considered statistically significant.

Results and discussion: It can be seen from Table 2 that 100% mice were dead at the cisplatin dose of 5 mg/kg, which was mainly due to the fact that such cisplatin dose could not suppress the rapid development of malignant ascites, so that the animal died of excess ascites. Cisplatin doses of 8 and 10 mg/kg could efficiently suppress the development of malignant ascites, whereas their prominent toxicity caused 100% and 75% of the mice to die respectively. After the co-administration of sodium selenosulfate, the death rates of the mice administrated with cisplatin doses of 8 and 10 mg/kg were reduced to 12.5% and 25% respectively, all the survival animals are cured, and no ascites was observed again 50 days later. During the treatment, the mice in cisplatin only group had gloomy fur, and behaved with piloerection and arched back, whereas after co-administration of sodium selenosulfate, the mice, especially those in the group with the dose of 8 mg/kg, had normal fur and no piloerection and arched back were observed.

The results showed that although the low doses of cisplatin, such as 5 mg/kg, with little toxicity was safer, it did not have good therapeutic efficacy, whereas high doses of cisplatin, such as 8 and 10 mg/kg, might have good therapeutic efficacy, but they had stronger toxicity, which may result in death. This is the real status of the current chemotherapy in clinic. Both the survival status and the survival rate showed that sodium selenosulfate reduced the toxicity of cisplation and enhance its therapeutic efficacy.

TABLE 2

Effect of sodium selenosulfate on the treatment of mice bearing H22 ascites with cisplatin

| Group | Death rate (%) | Survival time of dead mice (day) | Cure rate (%) |
|---|---|---|---|
| Control | 100 | 12 ± 1 (n = 8) | 0 |
| Cisplatin (5 mg/kg) | 100 | 20 ± 7* (n = 8) | 0 |
| Cisplatin (8 mg/kg) | 100 | 31 ± 12* (n = 8) | 0 |
| Cisplatin (10 mg/kg) | 75 | 21 ± 9 (n = 6) | 25 |
| Cisplatin (8 mg/kg)/Se(0.6 mg/kg) | 12.5 | 29 (n = 1) | 87.5 |
| Cisplatin (10 mg/kg)/Se(0.75 mg/kg) | 25 | 32 ± 12* (n = 2) | 75 |

Notes:
*means to compare with the control, p < 0.05; n represents the numbers of dead mice.

Example 5

Rapid Preparation of Sodium Selenosulfate by Using Sodium Selenite, Glutathione and Sodium Sulfite As illustrated above, sodium selenosulfate can be used to supplement selenium and enhance the therapeutic efficacy of chemotherapy agents, and the reliability for administration of Se is improved. However, there is a problem for applying sodium selenosulfate clinically in long term that sodium selenosulfate is unstable, and thus it must be prepared immediately prior to use. The known process for preparing sodium selenosulfate was to mix elemental selenium powder with sodium sulfite and to reflux a few hours at high temperature. Obviously, this process is not suitable to be used clinically. In order to obtain sodium selenosulfate easily, the present invention provides a process comprising the step of mixing sodium selefite, glutathione and sodium sulfite in a certain proportion.

Glutathione, which is a compound containing a mercapto group, was mixed with sodium selenite to form GS—Se—SG, which is stable under acidic condition and converted to elemental selenium under neutral or alkaline condition. After sodium sulfite was added into the mixture of sodium selenite and glutathione, the GS—Se—SG was converted to elemental selenium due to the alkalescence of sodium sulfite. Then, sodium sulfite rapidly reacted with the newly generated elemental selenium to form sodium selenosulfate immediately since the newly generated elemental selenium atom had not aggregated to form elemental selenium powder yet.

The solutions of 1 mM sodium selenite, glutathione and sodium sulfite were prepared respectively. One part of sodium selenite and 4 parts of glutathione were mixed homogeneously, and then 3 parts of sodium sulfite were added therein. Thus sodium selenosulfate was synthesized in 2-3 minutes at room temperature.

The above three prepared solutions might be cryopreserved at −20° C. and defrozen to mix homogeneously prior to use. Moreover, they can be freeze-dried as powder, which is dissolved with normal saline or water to be mixed homogeneously prior to use.

Example 6

Rapid Preparation of Sodium Selenosulfate by Using Sodium Selenite, Cysteine and Sodium Sulfite The solutions of 1 mM sodium selenite, 1 mM cysteine and sodium sulfite were prepared respectively. One part of sodium selenite and 10 parts of cysteine were mixed homogeneously, and then 30 parts of sodium sulfite were added therein. Thus sodium selenosulfate was synthesized in 2-3 minutes at room temperature.

As to such prepared three solutions, sodium selenite and cysteine can also be first mixed homogeneously and sodium sulfite was packaged separately. They were cryopreserved at −20° C., and defrozen to mix homogeneously prior to use.

Example 7

Rapid Preparation of Sodium Selenosulfate by Using Sodium Selenite, N-Acetyl Cysteine and Sodium Sulfite The solutions of 1 mM sodium selenite, 1 mM N-acetyl cysteine and sodium sulfite were prepared respectively. One part of sodium selenite and 4 parts of N-acetyl cysteine were mixed homogeneously, and then 20 parts of sodium sulfite were added therein. Thus sodium selenosulfate was synthesized in 2-3 minutes at room temperature.

As to such three prepared solutions, N-acetyl cysteine and sodium sulfite could be first mixed homogeneously and

Example 8

Rapid Preparation of Sodium Selenosulfate by Using Sodium Selenite, Lipoic Acid and Sodium Sulfite

The solutions of 1 mM sodium selenite, 1 mM lipoic acid and 1 mM sodium sulfite were prepared respectively. One part of sodium selenite and 6 parts of lipoic acid were mixed homogeneously, and then 20 parts of sodium sulfite were added therein. Thus sodium selenosulfate was synthesized in 2-3 minutes at room temperature.

As to such three prepared solutions, sodium selenite and sodium sulfite can be first mixed homogeneously and lipoic acid was packaged separately. They were cryopreserved at −20° C., and defrozen to mix homogeneously prior to use.

Example 9

Rapid Preparation of Sodium Selenosulfate by Using Sodium Selenite, Ascorbic Acid and Sodium Sulfite

Unlike the above examples which use reductive agents having a mercapto group, sodium selenite can also be reduced by a reductive agent without a mercapto group. The reductive agent may be ascorbic acid and the like, which do not have a mercapto group. It was mixed with sodium selenite to form elemental selenium. Since the elemental selenium had not aggregated to form elemental selemium powder yet, when sodium sulfite was added into the mixture of sodium selenite and the reductive agent, sodium sulfite and elemental selenium reacted rapidly to form sodium selenosulfate.

The solutions of 1 mM sodium selenite, 1 mM ascorbic acid and 1 mM sodium sulfite were prepared respectively. One part of sodium selenite and 0.3 part of ascorbic acid were mixed homogeneously, and then 4 parts of sodium sulfite were added therein. Thus sodium selenosulfate was synthesized in 2-3 minutes at room temperature.

The above three prepared solutions could be cryopreserved at −20° C., and defrozen to mix homogeneously prior to use. Moreover, they could be freeze-dried as powder, and dissolved with normal saline or water to be mixed homogeneously prior to use. In addition, ascorbic acid and sodium sulfite could be first mixed homogeneously and packaged, and sodium selenite could be packaged separately, and then they were mixed homogeneously prior to use. Further, sodium selenite and ascorbic acid could be mixed homogeneously and cryopreserved, and sodium sulfite may be packaged separately, and they were mixed homogeneously prior to use.

Example 10

Rapid Preparation of Sodium Selenosulfate by Using Sodium Selenite, Ascorbic Acid and Sodium Sulfite

The solutions of 1 mM sodium selenite, 1 mM ascorbic acid and 1 mM sodium sulfite were prepared respectively. One part of sodium selenite and 10 parts of ascorbic acid were mixed homogeneously, and then 30 parts of sodium sulfite were added therein. Thus sodium selenosulfate was synthesized in 2-3 minutes at room temperature.

Example 11

Rapid Preparation of Sodium Selenosulfate by Using Sodium Sulfite and Elemental Selenium in Nano Size

All the above processes, which use a reductive agent with or without a mercapto group, include a step of reducing sodium selenite to elemental selenium. When the reaction between the newly generated elemental selenium and sodium sulfite starts, the newly generated elemental selenium does not aggregated efficiently, so it is easy to obtain sodium selenosulfate rapidly. It has been reported that bovine serum albumin can prevent elemental selenium from aggregating, thus forming stable elemental selenium in nano size. Since the nano-sized elemental selenium has a much smaller size than the commercial elemental selenium powder, it can be reduced rapidly by sodium sulfite. Elemental selenium in nano size was first synthesized according to the process described in literature: sodium selenite was reduced to elemental selenium atom by using glutathione, and then into the redox system, was added a reagent having dispersing and absorbing functions, such as bovine serum albumin, which can control the newly generated elemental selenium atom to aggregate at nano level. The nano-sized elemental selenium with red color could be preserved at 2-8° C. for a long time, and keep its size and color substantially constant. Sodium sulfite (4 mM) was mixed with the elemental selenium (1 mM) with a size of 5-15 nm, which has been preserved more than one year, at a ratio of 1:1 in a water bath at 60° C. The red color of elemental selenium disappeared in one minute, which indicated the formation of sodium selenosulfate. As compared with elemental selenium powder, the reaction between the nano-sized elemental selenium and sodium sulfite is obviously very fast without refluxing at high temperature.

These processes ensured that fresh sodium selenosulfate could be obtained easily and rapidly, which makes it easy to apply sodium selenosulfate clinically for supplementing Se or enhancing the therapeutic efficacy of chemotherapy agents.

The above examples are only for illustration and they should not be construed to limit the scope of the present. In example 4, the therapeutic efficacy of chemotherapy agents can also be improved by sodium selenosulfate even though the chemotherapy agent is changed. In examples 5-10, sodium selenosulfate can also be formed rapidly even though the reductive agent is changed. For example, sodium selenosulfate can be formed by the following steps: introducing sulfur dioxide into sodium selenite, or adding sodium sulfite first, followed by the addition of acid to form sulfur dioxide; reducing sodium selenite to elemental selenium by sulfur dioxide; and after the formation of elemental selenium, adding sodium sulfite to reduce it to sodium selenosulfate. In examples 5-10, sodium selenosulfate can also be formed rapidly by changing the ratio of the reductive agent and sodium sulfite, and sodium selenosulfate will be stabilized longer if the concentration of sodium sulfite is increased. In example 11, when elemental seleniums with different nano sizes are used to react with sodium sulfite, both the reaction time and reaction temperature are reduced, as compared with the commercial elemental selenium powder. Obviously, these modifications are well known to the skilled person in the art based on the present invention.

The invention claimed is:

1. A method for enhancing the therapeutic efficacy of cisplatin for cancers by administering to a subject undergoing chemotherapy an effective amount of sodium selenosulfate.

2. The method according to claim 1, wherein the sodium selenosulfate is prepared by a rapid process comprising: mixing sodium selenite, reductive agent and sodium sulfite homogeneously in a proportion; and forming sodium selenosulfate in 2-3 minutes at room temperature, wherein the reductive agent is glutathione, cysteine, N-acetylcysteine, lipoic acid or ascorbic acid; based on molar ratio, sodium selenite is one part, the reductive agent is 0.3-10 parts and sodium sulfite is 3-30 parts.

3. The method according to claim 2, wherein sodium selenite, the reductive agent and sodium sulfite are optionally packaged separately, and they are mixed homogeneously prior to use.

4. The method according to claim 2, wherein any two among sodium selenite, the reductive agent and sodium sulfite are first mixed homogeneously and packaged, the third is packaged separately to be mixed homogeneously prior to use.

5. The method of claim 1, wherein the effective amount of sodium selenosulfate administered has a lower toxicity to normal tissues than the same amount of sodium selenite by weight selenium.

6. The method of claim 1, wherein the effective amount of sodium selenosulfate administered has a higher cytotoxicity to tumor cells than the same amount of sodium selenite by weight selenium.

7. The method of claim 6, wherein the effective amount of sodium selenosulfate administered has a higher cytotoxicity to human hepatoma cells HepG2 than the same amount of sodium selenite by weight selenium.

8. The method of claim 6, wherein the effective amount of sodium selenosulfate administered has a higher toxicity to human colorectal cancer cells CaCo2 than the same amount of sodium selenite by weight selenium.

* * * * *